US008541482B2

(12) United States Patent
Vu et al.

(10) Patent No.: US 8,541,482 B2
(45) Date of Patent: *Sep. 24, 2013

(54) REMOVABLE MULTILAYER NAIL COATING SYSTEM AND METHODS THEREFORE

(75) Inventors: Thong Vu, Vista, CA (US); Douglas D. Schoon, Dana Point, CA (US)

(73) Assignee: Creative Nail Design, Inc., Vista, CA (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/573,640

(22) Filed: Oct. 5, 2009

(65) Prior Publication Data

US 2011/0082228 A1  Apr. 7, 2011

(51) Int. Cl.
C08F 2/50 (2006.01)
C08G 18/08 (2006.01)
C03C 25/10 (2006.01)
A61F 13/15 (2006.01)

(52) U.S. Cl.
USPC ............... 522/64; 522/68; 522/90; 522/96; 522/120; 522/121; 522/182; 524/589; 524/599; 521/149

(58) Field of Classification Search
USPC ............... 522/64, 68, 90, 96, 120, 121, 182; 524/589, 599; 521/149
See application file for complete search history.

(56) References Cited

U.S. PATENT DOCUMENTS

| | | | |
|---|---|---|---|
| 1,548,497 A | 8/1925 | Weeks | |
| 1,743,922 A | 1/1930 | Kirlin | |
| 1,900,761 A | 3/1933 | Proteau | |
| 1,947,153 A | 2/1934 | Dellinger | |
| 2,979,061 A | 4/1961 | Greenman | |
| 3,297,664 A | 1/1967 | Miskel | |
| 3,629,187 A | 12/1971 | Waller | |
| 3,709,866 A | 1/1973 | Waller | |
| 3,928,113 A | 12/1975 | Rosenberg | |
| 4,089,763 A | 5/1978 | Dart | |
| 4,158,053 A * | 6/1979 | Greene et al. ............ | 424/61 |
| 4,174,307 A | 11/1979 | Rowe | |
| 4,189,365 A | 2/1980 | Schmitt | |
| 4,205,018 A | 5/1980 | Nagasawa | |
| 4,229,431 A | 10/1980 | Lee, Jr. | |
| 4,260,701 A | 4/1981 | Lee | |
| 4,421,881 A | 12/1983 | Benkendorf | |
| 4,424,252 A | 1/1984 | Nativi | |
| 4,514,527 A | 4/1985 | Bowen | |
| 4,521,550 A | 6/1985 | Bowen | |
| 4,572,888 A | 2/1986 | Maeda | |
| 4,574,138 A | 3/1986 | Moran | |
| 4,596,260 A | 6/1986 | Giuliano | |
| 4,600,030 A | 7/1986 | Newman | |
| 4,666,952 A | 5/1987 | Henne | |
| 4,682,612 A | 7/1987 | Giuliano | |
| 4,690,369 A | 9/1987 | Giuliano | |
| 4,692,396 A | 9/1987 | Uchida | |
| 4,704,303 A | 11/1987 | Cornell | |
| 4,718,957 A | 1/1988 | Sensenbrenner | |
| 4,721,735 A | 1/1988 | Bennett | |
| 4,745,003 A | 5/1988 | Sirkoch | |
| 4,766,005 A | 8/1988 | Montgomery | |
| 4,775,580 A | 10/1988 | Dighton | |
| 4,813,875 A | 3/1989 | Hare | |
| 4,844,102 A | 7/1989 | Repensek | |
| 4,846,165 A | 7/1989 | Hare | |
| 4,863,993 A | 9/1989 | Montgomery | |
| 4,867,680 A | 9/1989 | Hare | |
| 5,026,780 A | 6/1991 | Takizawa | |
| 5,063,257 A | 11/1991 | Akahane | |
| 5,071,888 A | 12/1991 | Kubota | |
| 5,118,495 A | 6/1992 | Nafziger | |
| 5,127,414 A | 7/1992 | Mast | |
| 5,173,288 A * | 12/1992 | Everhart et al. .......... | 510/118 |
| 5,177,120 A | 1/1993 | Hare | |
| 5,194,292 A | 3/1993 | Billings | |
| 5,206,011 A | 4/1993 | Pappas et al. | |
| 5,219,965 A | 6/1993 | Valint | |
| 5,229,431 A | 7/1993 | Pinchuk | |
| 5,270,351 A | 12/1993 | Bowen | |
| 5,314,683 A | 5/1994 | Schlossman | |
| 5,328,725 A | 7/1994 | Sato et al. | |
| 5,338,769 A | 8/1994 | Miyamoto | |
| 5,344,583 A | 9/1994 | Bayless | |
| 5,407,666 A | 4/1995 | Patel et al. | |

(Continued)

FOREIGN PATENT DOCUMENTS

EP  0356868 A2  3/1990
EP  0426085 A1  5/1991

(Continued)

OTHER PUBLICATIONS

Kumar, Sudesh G and Kalpagam, V and Nandi, US and Vasantharajan, VN (1981) Biodegradation of gelatin-g-Poly (ethyl Acrylate) copolymers, 26 Journal of Applied Polymer Science, 3633-3641.
Venz S, Dickens B, Modified Surface-Active Monomers for Adhesive Binding to Dentin, 72 J. Dental Research 582-6, (1993).
Cheremisinoff, N.P. "Handbook of Hazardous Chemical Properties," Copyright 2000, Elsevier, p. 211.
International Search Report for PCT International Application No. PCT/US2010/147171, mailed Nov. 10, 2010.
Physical Properties of Monomers, "Diurethane Dimethacrylate (isomers)." Polymer Handbook, 4th Edition, 1999, John Wiley & Sons.
International Search Report for PCT International Application No. PCT/US2011/027455, mailed May 9, 2011.

(Continued)

*Primary Examiner* — Michael Pepitone
*Assistant Examiner* — Jessica Roswell
(74) *Attorney, Agent, or Firm* — Venable LLP; Keith G. Haddaway

(57) ABSTRACT

The present disclosure relates generally to compositions for nail coatings, and particularly, but not by way of limitation, to polymerizable compositions. The disclosure further relates to methods of making a polymerizable, protective and scratch resistant topcoat layer that can be easily removed.

26 Claims, No Drawings

(56) References Cited

U.S. PATENT DOCUMENTS

| | | |
|---|---|---|
| 5,415,903 A | 5/1995 | Hoffman |
| 5,424,061 A | 6/1995 | Pappas et al. |
| 5,426,166 A | 6/1995 | Usifer |
| 5,435,994 A | 7/1995 | Valenty |
| 5,453,451 A | 9/1995 | Sokol |
| 5,456,905 A | 10/1995 | Valenty |
| 5,484,864 A | 1/1996 | Usifer |
| 5,516,509 A | 5/1996 | Marr-Leisy et al. |
| 5,637,292 A | 6/1997 | Thomas |
| 5,662,891 A | 9/1997 | Martin |
| 5,690,940 A | 11/1997 | Joo |
| 5,698,371 A | 12/1997 | Mirle et al. |
| 5,708,052 A | 1/1998 | Fischer |
| 5,720,804 A | 2/1998 | Marin |
| 5,785,958 A | 7/1998 | Sirdesai et al. |
| 5,792,447 A | 8/1998 | Socci |
| 5,824,373 A | 10/1998 | Biller |
| 5,848,853 A | 12/1998 | Clenet |
| 5,871,573 A | 2/1999 | Cook et al. |
| 5,958,951 A | 9/1999 | Ahrndt |
| 5,965,111 A | 10/1999 | Ellingson |
| 5,965,147 A | 10/1999 | Steffier |
| 5,985,951 A | 11/1999 | Cook |
| 5,985,998 A | 11/1999 | Sommerfeld |
| 5,994,530 A | 11/1999 | Posey-Dowty et al. |
| 5,998,495 A | 12/1999 | Oxman |
| 6,015,549 A | 1/2000 | Cowperthwaite |
| 6,020,402 A | 2/2000 | Anand |
| 6,121,381 A | 9/2000 | Deguchi |
| 6,147,137 A | 11/2000 | Jia |
| 6,238,679 B1 | 5/2001 | delaPoterie |
| 6,239,189 B1 | 5/2001 | Narayan |
| 6,251,520 B1 | 6/2001 | Blizzard et al. |
| 6,254,878 B1 | 7/2001 | Bednarek et al. |
| 6,255,034 B1 | 7/2001 | Shimada |
| 6,355,599 B1 | 3/2002 | Zahora |
| 6,391,938 B1 | 5/2002 | Lilley |
| 6,413,696 B1 | 7/2002 | Pang |
| 6,426,034 B1 | 7/2002 | McComas |
| 6,481,444 B1 | 11/2002 | Lilley |
| 6,599,958 B2 | 7/2003 | Lilley |
| 6,685,838 B2 | 2/2004 | Licata |
| 6,750,277 B1 | 6/2004 | Yamana et al. |
| 6,803,394 B2 | 10/2004 | Lilley et al. |
| 6,818,207 B1 | 11/2004 | Schoon et al. |
| 6,831,115 B2 | 12/2004 | Williams |
| 7,063,936 B2 | 6/2006 | Kakino |
| 7,098,256 B2 | 8/2006 | Ong |
| 7,125,591 B2 | 10/2006 | Nakajima et al. |
| 7,309,550 B2 | 12/2007 | Rach |
| 7,364,834 B2 | 4/2008 | Barr |
| 7,378,460 B2 | 5/2008 | Schmidt |
| 7,388,039 B2 | 6/2008 | Williams |
| 7,514,477 B2 | 4/2009 | Klare |
| 7,595,351 B2 | 9/2009 | Hayes |
| 7,615,283 B2 | 11/2009 | Radcliffe |
| 7,649,058 B2 | 1/2010 | McCabe |
| 7,713,680 B2 | 5/2010 | Ito |
| 7,718,264 B2 | 5/2010 | Klun |
| 7,722,939 B2 | 5/2010 | Schwantes |
| 7,806,050 B2 | 10/2010 | Nakamura |
| 8,367,742 B2 | 2/2013 | Vu et al. |
| 2001/0007676 A1 | 7/2001 | Mui et al. |
| 2002/0156144 A1 | 10/2002 | Williams et al. |
| 2003/0019501 A1 | 1/2003 | Hirota |
| 2003/0134932 A1 | 7/2003 | Lehmann |
| 2003/0175225 A1 | 9/2003 | Leacock et al. |
| 2003/0220416 A1 | 11/2003 | Montgomery |
| 2004/0249014 A1 | 12/2004 | Williams |
| 2005/0002878 A1 | 1/2005 | Lefrancois et al. |
| 2006/0005772 A1 | 1/2006 | Shin |
| 2006/0039939 A1 | 2/2006 | Lai |
| 2006/0128833 A1 | 6/2006 | Itoh et al. |
| 2006/0189728 A1 | 8/2006 | Qian |
| 2007/0021533 A1 | 1/2007 | Yan |
| 2007/0099119 A1 | 5/2007 | Rach |
| 2007/0106017 A1 | 5/2007 | Kessel et al. |
| 2008/0149270 A1 | 6/2008 | Oshima et al. |
| 2008/0167399 A1 | 7/2008 | Utterodt et al. |
| 2008/0213506 A1 | 9/2008 | Eu |
| 2008/0241083 A1 | 10/2008 | Schoon et al. |
| 2009/0086492 A1 | 4/2009 | Meyer |
| 2009/0220436 A1 | 9/2009 | Anderson et al. |
| 2010/0012263 A1 | 1/2010 | Oshima |
| 2010/0105289 A1 | 4/2010 | Yonezu et al. |
| 2011/0045036 A1 | 2/2011 | Lintner et al. |

FOREIGN PATENT DOCUMENTS

| | | |
|---|---|---|
| EP | 0453628 | 10/1991 |
| EP | 0545116 A2 | 6/1993 |
| EP | 943310 | 3/2002 |
| EP | 1479364 A1 | 11/2004 |
| EP | 1450755 B1 | 8/2008 |
| GB | 656264 | 8/1951 |
| JP | 5271460 A | 10/1993 |
| KR | 970002606 | 3/1997 |
| WO | 9312759 A1 | 7/1993 |
| WO | 9848769 A1 | 11/1998 |
| WO | 9955290 | 11/1999 |
| WO | 0236637 A1 | 5/2002 |
| WO | 2004030801 A1 | 4/2004 |
| WO | 2008082929 A2 | 7/2008 |
| WO | 2009005975 A1 | 1/2009 |
| WO | 2011011304 A2 | 1/2011 |

OTHER PUBLICATIONS

International Search Report for PCT International Application No. PCT/US2010/047165, mailed Feb. 25, 2011.
Notice of Allowance issued in U.S. Appl. No. 13/079,261 dated Dec. 26, 2012.
Restriction Requirement issued in U.S. Appl. No. 13/042,436 dated Jan. 10, 2013.
New Zealand Examination Report dated Nov. 13, 2012, issued in New Zealand Patent Application No. 599505.
New Zealand Examination Report dated Nov. 13, 2012, issued in New Zealand Patent Application No. 599293.
Data Sheet for Diurethane Dimethacrylate from Esstech, Inc., 2011.
Data Sheet for Polypropylene Glycol Monomethacrylate. Sartomer. 2011.
Ebecryl 200 Data Sheet. Lookchem. 2008.
International Preliminary Report on Patentability issued in International Application No. PCT/US2010/047169 dated Apr. 11, 2012.
International Preliminary Report on Patentability issued in International Application No. PCT/US2010/074165 dated Mar. 13, 2012.
International Preliminary Report on Patentability issued in International Application No. PCT/US2010/074171 dated Apr. 11, 2012.
International Search Report for PCT International Application No. PCT/US2010/147169 dated Sep. 11, 2010.
Office Action issued in U.S. Appl. No. 12/555,571 dated May 17, 2011.
Office Action issued in U.S. Appl. No. 12/555,571 dated Oct. 26, 2011.
Office Action issued in U.S. Appl. No. 12/573,633 dated Feb. 13, 2012.
Office Action issued in U.S. Appl. No. 12/573,633 dated May 24, 2011.
Office Action issued in U.S. Appl. No. 13/079,261 dated Jun. 14, 2012.
Office Action issued in U.S. Appl. No. 13/079,261 dated Oct. 14, 2011.
Office Action issued in U.S. Appl. No. 13/303,584 dated Oct. 22, 2012.

* cited by examiner

US 8,541,482 B2

REMOVABLE MULTILAYER NAIL COATING SYSTEM AND METHODS THEREFORE

FIELD OF THE INVENTION

The present disclosure relates generally to compositions for nail coatings, and particularly, but not by way of limitation, to polymerizable compositions. The disclosure further relates to methods of making a polymerizable topcoat layer.

BACKGROUND

The information provided below is not admitted to be prior art to the present invention, but is provided solely to assist the understanding of the reader.

Artificial fingernail and toenail compositions in the form of nail coatings and extenders are well known and have become a major product line in the appearance and beauty industry. The appearance of one's fingernails (and in many cases also toenails) has become of importance to many fashion conscious individuals. Commercial artificial nail compositions have been used to enhance the appearance of nails and also to enhance the physical properties of nails, including strengthening fragile nail surfaces.

Conventional nail coatings may be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of long lasting, highly durable cross-linked thermoset nail coating that is difficult to remove. Artificial nails may possess greatly enhanced adhesion, durability, as well as scratch and solvent resistance when compared to nail polishes. However, because of these inherent properties, such reactive thermosets are much harder to remove, should the consumer so desire. Removal typically requires soaking in non-reactive solvents for 30-90 minutes (for acrylics and currently available "soakable gels"; it may take more than 90 minutes if ever to remove traditional UV nail gels by solvent) and typically may also require heavily abrading the surface or scraping with a wooden or metal probe to assist the removal process.

A nail coating system typically comprises three layers: a basecoat, a color layer, and a topcoat. The principle function of the basecoat is to provide adhesion to the natural nail. The color layer is applied over the basecoat. The second, or "color" layer may be colorless or translucent. Typically, it is colored and will have some opacity. The main function of the color layer is cosmetic and, in some cases, to enhance the durability of the whole nail. The final layer is applied on top of the color layer. This layer, normally called "topcoat," typically functions to provide shine to the finished nail coating composite. Moreover, the topcoat also function as a means of protecting the "color" layer from chemical (such as water or household products) and/or physical (such as UV light and) exposure as well as abrasion resistance.

Like other layers, topcoat can be of nail polish type (air-dry) or UV gel type (Light-cured). In general, the first type loses its shine relatively quickly (5 days or less.) It has low scratch resistance and low solvent resistance. The second type maintains its shine for a longer time (3 weeks or more) because it has relatively higher scratch and solvent resistances. On the other hand, the air-dry type topcoat is very easily removed by solvent whereas the light-cured version has almost no solvent removability. There has been a need for a topcoat that has relatively high scratch and solvent resistance that also has some degree of removability by solvent.

Conventional artificial nails comprise reactive monomers, and/or oligomers, and/or polymers, typically at 100% solids in the absence of non-reactive solvents. Upon application, of an "acrylic" type enhancement, (or after exposure of UV light to a "gel" type enhancement), a chemical reaction ensues resulting in the formation of a cross-linked thermoset. Artificial nail systems may possess enhanced adhesiveness and scratch resistance as compared to polishes. However, because of these enhanced properties, the thermoset is much harder to remove when the consumer so desires. Removal typically requires soaking in solvents for 30-90+ minutes and may also require abrasion on the topcoat and/or the color, and scraping or abrasion of the natural nail surface.

There remains a need for a nail coating system that possess the enhanced adhesion and durability properties of thermosets and also exhibits shorter and easier removal.

The present disclosure forms part of a nail covering system comprising a basecoat adhesion layer (application Ser. No. 12/555,571), an intermediate, decorative color layer (application Ser. No. 12/573,633), and the present application, a protective topcoat (application Ser. No. 12/573,640). The contents of each application are mutually incorporated into each of the others by reference for all purposes.

Other objects and advantages will become apparent from the following disclosure.

SUMMARY OF INVENTION

Aspects of the present disclosure when taken in conjunction with the related disclosures provide a basecoat characterized by firm adhesion to a nail surface combined with a solvent-induced "unzipping," "quick-release" feature that affords facile removal. Aspects of the present disclosure when taken in conjunction with the related disclosures provide a color layer characterized by firm adhesion to polymer surfaces combined with a solvent-induced "unzipping," "quick-release" feature that affords facile removal. Further aspects of the present disclosure when taken in conjunction with the related disclosures provide a protective topcoat characterized by firm adhesion to polymer surfaces combined with a solvent-induced "unzipping," "quick-release" feature that affords facile removal.

Aspects of the disclosure relate to a UV-curable composition for cosmetic topcoat application to nails or nail coatings comprising at least one UV-curable material (a UV-curable monomer, and/or UV-curable oligomer), at least one photoinitiator, at least one non-polymerizable, solvent-dissolvable resin, and at least one non-reactive solvent.

An aspect of the present disclosure provides a nail topcoat comprising a 3-dimensional (3-D) thermoset lattice interpenetrated by a network comprising an organic solvent-dissolvable resin. According to an aspect of the disclosure, the 3-D thermoset lattice provides the enhanced adhesion, toughness, and scratch-resistance typically associated with conventional artificial nails. According to an aspect of the disclosure, an interconnected system of voids and an interpenetrating network of an organic solvent-dissolvable resin provides ease of removal using solvent.

According to an aspect, the present disclosure provides a liquid composition comprising at least one UV-curable monomer, and/or oligomer, and/or polymer which polymerize to a 3-D thermoset. According to an aspect, the present disclosure provides a liquid composition comprising at least one organic solvent-dissolvable resin. According to an aspect, the organic solvent-dissolvable resin forms a network of inclusions within the 3-D thermoset lattice.

According to aspects of the disclosure, at least one UV-curable monomer is a (meth)acylate. As would be understood by persons skilled in the polymerization arts, the term (meth) acrylate refers to acrylates and/or methacrylates. According to aspects of the disclosure, the UV-curable monomer may be a single or mixed acrylate, a single or mixed methacrylate, or a mixture of acrylates and methacrylates.

According to an aspect, the present disclosure provides a monomer which confers the "unzipping" property of ease of removal of the polymerized lattice. According to an aspect, the monomer may be polypropylene glycol-4-monomethacrylate (PPG4 monomethacrylate). According to an aspect, suitable monomers may include any acrylated or methacrylated monomer in the PPG or polyethylene glycol (PEG) families. According to an aspect, the "unzipping" monomers are present at from about 0 to about 70 weight % (wt %).

According to an aspect, the liquid composition comprises reactive monomers, and/or oligomers, and/or polymers which provides the polymerized composition increased adhesiveness. According to an aspect, such reactive monomers, and/or oligomers, and/or polymers may be a (meth)acrylate. According to an aspect, such reactive monomers, and/or oligomers, and/or polymers may be selected from the group consisting of hydroxyethylmethacrylate (HEMA), hydroxypropylmethacrylate (HPMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacrylate (AAEMA), and mixtures thereof. According to an aspect, such reactive monomers, and/or oligomers, and/or polymers possess acidic functionality. According to an aspect, the monomer, oligomer or polymer which provides the polymerized composition increased adhesiveness is present from about 0 to about 50 wt %.

An aspect of the present disclosure provides a polymerizable liquid composition comprising a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. According to a further aspect, the ingredient which provides for ease of removal may be present at from about 0.1 to about 75 wt %.

Certain embodiments of the formulation may optionally comprise resins, such as, but not limited to polyvinylbutyral and/or tosylamide formaldehyde resins. Such resins act as film formers, adhesion promoters, and aids to removal. These resins may also qualify as solvent-dissolvable, interpenetrating resins which can be extracted to create channels for solvent absorption and migration.

According to an aspect of the disclosure, topcoat compositions may comprise up to 1 wt % of conventional pigments and/or dyes.

According to another aspect of the disclosure, the topcoat compositions may comprise up to 10 wt % of "effect pigment." As is known in the art, a metallic effect pigment may be a dispersion of finely-divided metals and/or alloys which may be used for decorative and/or protective purposes. As is known in the art an effect pigment may be a nacreous or pearlescent pigment and may comprise a dispersion of mica particles coated with a metal oxide layer. Pearlescent pigments may impart an iridescent, pearly sheen to coatings.

An aspect of the present disclosure provides methods of removal. According to an aspect, the thermoset polymerized from the disclosed composition provides a sensitivity to organic solvents and, in particular, to acetone. According to an aspect of the disclosure, means are provided to distribute organic solvent to the polymer/natural nail interface. According to an aspect, delivering an appropriate solvent to the polymer/natural nail interface will result in an unzipping effect which leads to rapid disruption of the adhesive bond interface and greatly facilitates quick and gentle removal from the natural nail.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BRIEF DESCRIPTION OF DRAWINGS

Not Applicable.

DETAILED DESCRIPTION OF A PREFERRED EMBODIMENT

Nail coatings commonly consist of a layer of material applied to a keratin nail surface. Prior art coatings may damage the nail by at least two mechanisms. First, adequate adhesion of the material to the nail may require abrasion to roughen the nail surface. And second, removal of the material may require prolonged exposure to possibly damaging solvents and or further abrasion of the nail surface.

An embodiment of the present disclosure provides a nail coating comprising a 3-dimensional (3-D) thermoset lattice interpenetrated by a network comprising an organic solvent-dissolvable resin. According to an aspect of the disclosure, a 3-D thermoset lattice provides the enhanced adhesion, toughness, and scratch-resistance of conventional artificial nails. According to an embodiment, a color layer may be interposed between the basecoat and the present topcoat layer.

An embodiment of the liquid composition comprises reactive monomers, and/or oligomers, and/or polymers which provides the polymerized composition increased toughness and scratch-resistance. In certain embodiments, such reactive monomers, and/or oligomers, and/or polymers may be a (meth)acrylate. As is known to persons of skill in the polymer arts, the term (meth)acrylate encompasses acrylates and/or methacrylates.

According to an aspect, such reactive monomers, and/or oligomers, and/or polymers may be selected from the group consisting of hydroxypropyl methacrylate (HPMA), hydroxyethyl methacrylate (HEMA), EMA, THFMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacylate (AAEMA), and mixtures thereof. According to an aspect, such reactive monomers, and/or oligomers, and/or polymers may possess acidic functionality. According to an aspect, the monomer, oligomer or polymer which provides the polymerized composition increased adhesiveness is present from about 0 to about 50 wt %.

Certain embodiments of the liquid composition comprise at least one monomer which confers the "unzipping" property by imparting to the interfacial bonds a sensitivity to organic solvent According to an aspect, the at least one monomer may be polypropylene glycol-4-monomethacrylate (PPG4 monomethacrylate). According to an aspect, suitable monomers may include any acrylated or methacrylated monomer in the PPG or polyethylene glycol (PEG) family. According to an aspect, the "unzipping" monomers are present at from about 0 to about 70 weight % (wt %).

An embodiment of the present disclosure provides a polymerizable liquid composition comprising a methacrylate monomer which provides improved adhesion, viscosity, wear and durability. In certain embodiments, the methacrylate monomer is a tetrahydrofurfural methacrylate. In other embodiments, some or all of the tetrahydrofurfural methacrylate may be substituted by such monomers including, but not limited to ethyl methacrylate (EMA), HPMA, and other monomers such as pyromellitic dianhydride glyceryl dimethacrylate, and similar (meth)acrylate monomers. The methacrylate monomer may be present from about 0 to about 70 wt %.

Certain embodiments of the polymerizable liquid composition of the present disclosure may comprise a urethane (meth)acrylate resin which may convey flexibility and toughness to the polymerized product. In certain embodiments, urethane methacrylates are preferred. The urethane (meth) acrylate monomer may be present from about 0 to about 50 wt %. In certain embodiments, the urethane (meth)acrylate may have a molecular weight (grams/mole) of from about 100 to about 20,000. In certain embodiments, the urethane (meth) acrylate may have a molecular weight of from about 300 to about 15,000. In certain embodiments, the urethane (meth) acrylate may have a molecular weight of from about 500 to about 13,000. In certain embodiments, the urethane (meth) acrylate may have a molecular weight of from about 500 to about 6,000.

In certain embodiments of the disclosure, the 3-D thermoset lattice is interpenetrated by a network of voids. Upon cure of the reactive components, some of these voids are filled with a non-reactive, organic solvent-dissolvable resin. When it is desired to remove the nail covering, the polymer is exposed to a solvent which dissolves solvent-dissolvable resin. Dissolution of the resin leaves a network of voids which fill with solvent. The voids channel the solvent to the interior of the thermoset and also to the polymer/nail interface.

Certain embodiments of the polymerizable liquid composition of the present disclosure may comprise a non-reactive, solvent-dissolvable polymer. According to an aspect, the non-reactive, solvent-dissolvable polymer is a cellulose ester.

According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. The non-reactive, solvent-dissolvable polymer may be a mixture of any acceptable polymer. According to a further aspect, the non-reactive, solvent-dissolvable polymer may be present at from about 0.1 to about 75 wt %.

Certain embodiments of the formulation may optionally comprise resins, such as, but not limited to polyvinylbutyral and/or tosylamide formaldehyde resins. Such resins may act as film formers, adhesion promoters, and aids to removal. These resins may also qualify as solvent-dissolvable, interpenetrating resins which can be extracted to create channels for solvent absorption and migration.

Without being bound by theory, the present invention's relative ease of removal of the nail covering was increased through facilitating entrance of solvent into the interior of the coating. Conventional polymerized nail coatings are weakened by long-term (30 to 90 minute) exposure to organic solvents. The solvent slowly seeps in at the outer surface and edges of the thermoset and eventually swells the coating. The swelling eventually weakens the entire matrix structure, as well as disrupts adhesion to the nail surface. Even a weakly attached nail coating may require abrasion to enhance solvent penetration and speed removal. However, the slow rate at which solvent diffuses through the thermoset, limits the rate of swelling.

The present invention provides a 3-D thermoset interpenetrated by a network of solvent-dissolvable channels and inclusions. Upon exposure to organic solvent, the cellulose ester, or other non-reactive, organic solvent-soluble polymer, is dissolved and leached from the coating. The result is a series of solvent accessible passageways riddled throughout the thermoset. Under these conditions, solvent may attack the interior of the thermoset no longer limited by a slow diffusion rate.

The inventive composition may be polymerizable with actinic radiation. The actinic radiation may be ultraviolet (UV) radiation. The UV radiation may be characterized by wavelengths of from about 320 to 420 nanometers.

After the liquid composition is applied to a surface, especially a polymer surface, the liquid may be cured by a UV-initiated, free-radical polymerization method. Persons of skill in the polymerization arts may readily determine suitable photoinitiators for use with the invention. Set forth below are non-limiting representative photoinitiators that are suitable for purposes of the invention.

Suitable, photoinitiators include, but are not limited to benzoyldiphenylphosphinates, phenyl ketones, and dimethyl ketals.

A non-limiting suitable photoinitiator is a 2,4,6-trimethyl-benzoyldiphenylphosphorous derivative. A suitable derivative is ethyl-2,4,6-trimethylbenzoyldiphenylphosphinate, which may be obtained under the tradename Lucirin® TPO-L (BASF Aktiengesellschaft, Ludwigshafen, DE). Another non-limiting suitable derivative is 2,4,6-Trimethylbenzoyl-diphenylphosphine oxide, which may be obtained under the trade name Lucerin® (BASF) or as Genocure® TPO (Rahn) The 2,4,6-trimethylbenzoyldiphenylphosphinate photoinitiator may be present from about 0% to about 20 wt %.

A non-limiting suitable phenyl ketone is hydroxycyclohexyl phenyl ketone, which may be obtained under the tradename Igracure® 184 (Ciba) and which may be present from about 0 to about 20 wt %.

A non-limiting suitable dimethyl ketal is benzil dimethyl ketal (BDK), which may be obtained under the tradename FIRSTCURE® BDK (Albemarle, Baton Rouge, La. US) and which may be present from about 0 to about 20 wt %.

Embodiments of the topcoat disclosure may comprise up to 1 wt % of conventional pigments and or dyes. Certain embodiments may comprise up to 10 wt % of effect pigments.

A conventional thermoset nail coating comprises 100% solids and does not comprise non-reactive solvents. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable non-reactive solvents may be selected from the group consisting of acetone, ethyl acetate, butyl acetate, isopropyl alcohol, ethanol, methyl ethyl ketone, toluene, hexane, and mixtures thereof. A particularly suitable non-reactive solvent is acetone. Typically a non-reactive solvent or a mixture of non-reactive solvents is included at up to about 70 weight percent. The present list is illustrative of suitable non-reactive solvents and is non-limiting.

Certain embodiments of the formulation may optionally comprise (meth)acrylic acid monomers and/or polymers in order to fine tune toughness and scratch-resistance properties. Non-limiting examples of such (meth)acrylates include: mono or poly(meth)acrylates, HPMA, HEMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, ethyl methacrylate, tetrahydrofurfuryl methacrylate, butyl methacrylate, isobutyl methacrylate, PEG-4 dimethacrylate, PPG monomethacrylate, trimethylolpropane trimethacrylate, hydroxyethyl methacrylate, isopropylidenediphenyl bisglycidyl methacrylate, lauryl methacrylate, cyclohexyl methacrylate, hexyl methacrylate, urethane methacrylate, hydroxypropyl methacrylate, triethylene glycol dimethacrylate, ethylene glycol dimethacrylate, tetraethylene glycol dimethacrylate, trimethylolpropane trimethacrylate, neopentylglycol dimethacylate.

Certain embodiments of the formulation may optionally comprise resins, such as, but not limited to polyvinylbutyral and/or tosylamide formaldehyde resins. Such resins act as film formers, adhesion promoters, and aids to removal.

Certain embodiments of the formulation may optionally comprise plasticizers, such as, but not limited to diisobutyl adipate. Plasticizers act to minimize the effect of brittleness of the subsequently formed polymer after exposure to UV radiation, sun light, and air. Plasticizers also are found to slightly shorten the removal time. Plasticizers may be present at from 0 to about 25 wt %.

As compared to conventional nail coatings, the present disclosure relates to a major advantage in that it enables the durable color layer to adhere to the natural nail for periods in excess of two weeks without breakdown of the coating. In contrast to conventional coatings, the present disclosure relates to a UV gel system that is non-damaging to the natural nail. The application process requires no abrasive treatment of the nail, and the process of removal does not require abrasive treatment on this topcoat layer. Moreover, in comparison to conventional systems, the present disclosure relates to a more rapidly removable (meth)acrylate polymer system achieving removal in less than 20 minutes for the whole system.

INDUSTRIAL UTILITY

This invention has industrial applicability in providing compositions and methods for making cosmetic protective nail topcoats that are tough, durable, semi-chemical resistant, semi-scratch resistant, and still provide means for removing a nail coating without requiring abrasion.

EXAMPLE 1

Chemical Resistance Test

To compare chemical resistance a topcoat formulation according to the present disclosure was compared against a commercial polish topcoat formulation and a commercial enhancement type topcoat formulation. We employed the conventional MEK double rub test except that acetone substituted for the methyl ethyl ketone. Thin films of each formulation were prepared on glass microscope slides. Each film was formed to a 5 mil wet thickness. The commercial enhancement type formulation and the formulation of the present disclosure were cured by exposure to UV light using a Brisa™ lamp. A very thin, unpolymerized tacky top layer was wiped to dryness using 99 wt % isopropanol. The polish formulation was not cured. All specimens were aged under conditions of ambient light and temperature for 24 hours. Following aging, each sample was individually rubbed with cotton pads soaked in 99 wt % acetone. The polish formulation was completely removed by two rubs. The formulation of the present invention was dulled by two rubs, but remained intact for at least 150 rubs. The enhancement formulation remained shiny and intact for at least 200 rubs.

EXAMPLE 2

Pencil Hardness Test

To test scratch resistance, we recorded the lowest "H" number of the pencil which dented test samples prepared as given in Example 1. We also recorded the lowest "H" number of the pencil capable of tearing test films. The polish formulation was dented and torn by 3H and 4H pencils, respectively. The formula of the present disclosure was dented and torn respectively by 3H and 6H pencils. The enhancement formula was not torn by any tested pencil and was dented by a 4H pencil.

The invention claimed is:

1. A multilayer nail covering system comprising at least a first layer and a second layer,
    wherein at least one of the first and second layer is curable to an acrylic thermoset lattice layer covering a nail surface upon exposure to actinic radiation;
    wherein at least one of the first or second layer comprises:
    hydroxypropyl methacrylate (HPMA),
    at least one reactive urethane (meth)acrylate, and
    a sufficient amount of a non-reactive, solvent-dissolvable polymer and a non-reactive solvent such that, when cured to the nail surface, the system is removable from the nail surface within 20 minutes of exposure to organic solvent.

2. The nail covering system of claim 1, wherein the at least one layer further comprises hydroxyethylmethacrylate (HEMA).

3. The nail covering system of claim 1, wherein said non-reactive, solvent-dissolvable polymer is a cellulose ester.

4. The nail covering system of claim 3, wherein said cellulose ester is a cellulose acetate alkylate.

5. The nail covering system of claim 4, wherein said cellulose acetate alkylate is selected from the group consisting of cellulose acetate butyrate, cellulose acetate propionate, and mixtures thereof.

6. The nail covering system of claim 1, wherein said non-reactive solvent is selected from the group consisting of ketones, alkyl acetates, alcohols, alkanes, alkenes, and mixtures thereof.

7. The nail covering system of claim 1, wherein said non-reactive solvent is selected from the group consisting of acetone, ethyl acetate, butyl acetate, isopropyl alcohol, ethanol, methyl ethyl ketone, toluene, hexane, and mixtures thereof.

8. The nail covering system of claim 1, wherein the at least one layer further comprises at least one photoinitiator.

9. The nail covering system of claim 8, wherein said at least one photoinitiator is selected from the group consisting of benzoylphenylphosphinates, cyclohexylphenyl ketones, benzyl ketals, and mixtures thereof.

10. The nail covering system of claim 9, wherein said at least one photoinitiator is selected from the group consisting of 2,4,6-trimethylbenzoyldiphenylphosphinate, hydroxycyclohexyl phenyl ketone, benzyl dimethyl ketal, and mixtures thereof.

11. The nail covering system of claim 1, wherein the at least one layer further comprises at least one addition-polymerizable, ethylenically-unsaturated monomer.

12. The nail covering system of claim 1, wherein upon exposure to actinic radiation, the at least one layer cures to an acrylic thermoset lattice layer having voids defined therein, wherein at least a portion of said voids contain said at least one non-reactive, solvent-dissolvable polymer.

13. The nail covering system of claim 1, wherein said non-reactive, solvent-dissolvable polymer is present at from about 5 to about 90 wt %.

14. The nail covering system of claim 1, wherein said non-reactive, solvent-dissolvable polymer is present at from about 20 to about 80 wt %.

15. The nail covering system of claim 1, wherein said non-reactive, solvent-dissolvable polymer is present at from about 30 to about 70 wt %.

16. The nail covering system of claim 1, wherein the organic solvent is acetone.

17. The nail covering system according to claim 1, wherein the at least one layer further comprises an adhesion-promoting (meth)acrylate.

18. The nail covering system according to claim 17, wherein said adhesion-promoting (meth)acrylate is selected from the group consisting of tetrahydrofurfural methacrylate, ethyl methacrylate, pyromellitic dianhydride glyceryl dimethacrylate, and mixtures thereof.

19. The nail covering system according to claim 1, wherein the at least one layer further comprises pyromellitic glyceryl dimethacrylate.

20. The nail covering system according to claim 1, wherein the at least one layer further comprises at least one polyalkylene glycol mono(meth)acrylate.

21. The nail covering system according to claim 20, wherein said at least one polyalkylene glycol mono(meth)acrylate is a compound selected from the group consisting of polypropylene glycol monomethacrylates, polyethylene glycol monomethacrylates, and mixtures thereof.

22. The nail covering system of claim 1, wherein said at least one urethane (meth)acrylate has a molecular weight of from about 300 to about 1,000.

23. The nail covering system of claim 1, wherein the at least one layer further comprises at least one plasticizer having the general structure RCO—OR' where RCO— represents a carboxylic acid radical, where —OR' is an alcohol residue, and where R and R' are fatty radicals having 6 to 30 saturated or unsaturated carbon atoms.

24. The nail covering system according to claim 1, wherein the at least one layer further comprises a reactive (meth)acrylate monomer or polymer selected from the group consisting of: hydroxyethylmethacrylate (HEMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacylate (AAEMA), and mixtures thereof.

25. The nail covering system according to claim 1, having a hardness of at least 3H on the pencil hardness test.

26. A nail covering system comprising: a basecoat layer; an intermediate layer; and a topcoat layer; wherein at least one layer comprises:
 (a) hydroxypropyl methacrylate (HPMA);
 (b) at least one reactive urethane (meth)acrylate;
 (c) at least one non-reactive, solvent-dissolvable polymer; and
 (d) at least one non-reactive solvent; and
 wherein, upon exposure to actinic radiation, the at least one layer cures to an acrylic thermoset lattice layer covering a nail surface.

* * * * *